United States Patent [19]

Yamada et al.

[11] Patent Number: 4,839,018
[45] Date of Patent: Jun. 13, 1989

[54] AIR/FUEL RATIO DETECTOR

[75] Inventors: Tetsusyo Yamada; Sadao Ichikawa, both of Aichi, Japan

[73] Assignees: NGK Spark Plug Co., Ltd., Aichi; Mitsubishi Denki Kabushiki Kaisha, Tokyo, both of Japan

[21] Appl. No.: 150,468

[22] Filed: Feb. 1, 1988

Related U.S. Application Data

[63] Continuation of Ser. No. 807,086, Dec. 10, 1986, abandoned.

[30] Foreign Application Priority Data

Dec. 11, 1984 [JP]  Japan .................................. 59-261314

[51] Int. Cl.⁴ ............................................ G01N 27/46
[52] U.S. Cl. ..................... 204/425; 204/426; 204/427
[58] Field of Search .................... 204/1 S, 421–429

[56] References Cited

U.S. PATENT DOCUMENTS

| | | | |
|---|---|---|---|
| 4,207,159 | 6/1980 | Kimura et al. | 204/425 |
| 4,568,443 | 2/1986 | Asayama et al. | 204/425 |
| 4,579,643 | 4/1986 | Mase et al. | 204/425 |
| 4,586,476 | 5/1986 | Asayama et al. | 204/426 |

Primary Examiner—T. Tung
Attorney, Agent, or Firm—Sughrue, Mion, Zinn, Macpeak & Seas

[57] ABSTRACT

An A/F detector having an output which is unambiguous over the entire operating region of the device, including both fuel-rich and fuel-lean regions. The detector includes two cells, an electrochemical cell and a pump cell. A constant current is passed through the electrochemical cell and the current through the pump cell is controlled in such a manner that the voltage across the electrochemical cell is constant. The current through the pump cell is detected to provide the unambiguous output signal.

14 Claims, 4 Drawing Sheets

AIR/FUEL RATIO DETECTOR

This is a continuation of application Ser. No. 807,086 filed Dec. 10, 1985, now abandoned.

BACKGROUND OF THE INVENTION

The present invention relates to an apparatus for detecting the A/F (air/fuel) ratio of an exhaust gas from a burner device such as an internal combustion engine on the basis of the concentration of oxygen contained in the exhaust.

Many systems have been proposed for detecting the A/F ratio of a combustion mixture supplied on a burner device such as an internal combustion engine on the basis of the concentration of oxygen in the exhaust gas. In a system described in Unexamined Published Japanese Patent Application No. 178354/1984, two elements are provided, each in the form of an oxygen-ion-conductive solid-electrolyte plate having a porous electrode formed on both sides, with the two plates disposed facing each other with a small gap therebetween. One of the elements is used as an oxygen pump cell for pumping oxygen out of the gap, while the other element is used as an oxygen-concentration-difference-actuated electrochemical sensor cell for generating a voltage in response to the difference between the concentration of oxygen in the ambient atmosphere and that in the gap. The system is capable of producing an accurate A/F ratio indicating signal at least in the fuel-lean region.

This A/F ratio detector, however, has the characteristic shown in FIG. 2. The system is primarily intended for generating an A/F ratio indicating signal in the fuel-lean region where residual oxygen is present in the exhaust gas, but even in the fuel-rich region where no residual oxygen is present, the system responds to CO, $CO_2$, $H_2O$, etc., in the exhaust, producing a signal identical to that generated in the fuel-lean region. In other words, two values of A/F ratio are possible for the same value of the detection signal. In order to avoid this ambiguity, the system can be employed for A/F ratio control purposes only when it is definitely known whether the controlled burner device is operating in the fuel-lean or fuel-rich region. In the graph of FIG. 2, $\lambda$ denotes the excess air ratio, $\lambda = 1$ indicating an A/F ratio equal to the theoretical value.

SUMMARY OF THE INVENTION

Accordingly, an object of the present invention is to provide an A/F ratio detector that is capable of producing an A/F ratio detection signal in the form of a unidirectional, unambiguous electrical quantity whether the burner device is operating in the fuel-lean region, at the theoretical A/F ratio, or in the fuel-rich region. Such a detection signal may be used directly for performing A/F ratio control, which can then be done precisely and quite easily over the entire A/F range.

The above-stated object of the present invention can be achieved by an A/F ratio detector comprising: (1) a sensor unit composed of two elements, each consisting of an oxygen ion-conductive solid electrolyte having a porous electrode formed on both surfaces and which are disposed facing a diffusion compartment which receives a limited inflow of exhaust gas, and (2) A/F ratio signal detecting means that operates one of the two elements as an oxygen-concentration-difference-actuated electrochemical cell and the other as an oxygen pump and which controls the voltage produced by the electrochemical cell or the current flowing into the oxygen pump so as to produce an A/F ratio signal indicative of the concentration of oxygen in the exhaust gas. The detector is characterized in that the sensor unit is provided with an air compartment so that at least the electrochemical cell contacts the atmosphere at the electrode disposed opposite to the side facing the diffusion compartment. The detector is further characterized in that constant current supply means for supplying a predetermined amount of current to the electrochemical cell is provided in the A/F ratio signal detecting means so that oxygen is pumped at a predetermined rate from the atmosphere into said diffusion compartment by said electrochemical cell.

DESCRIPTION OF THE PREFERRED EMBODIMENTS

Figure 1:
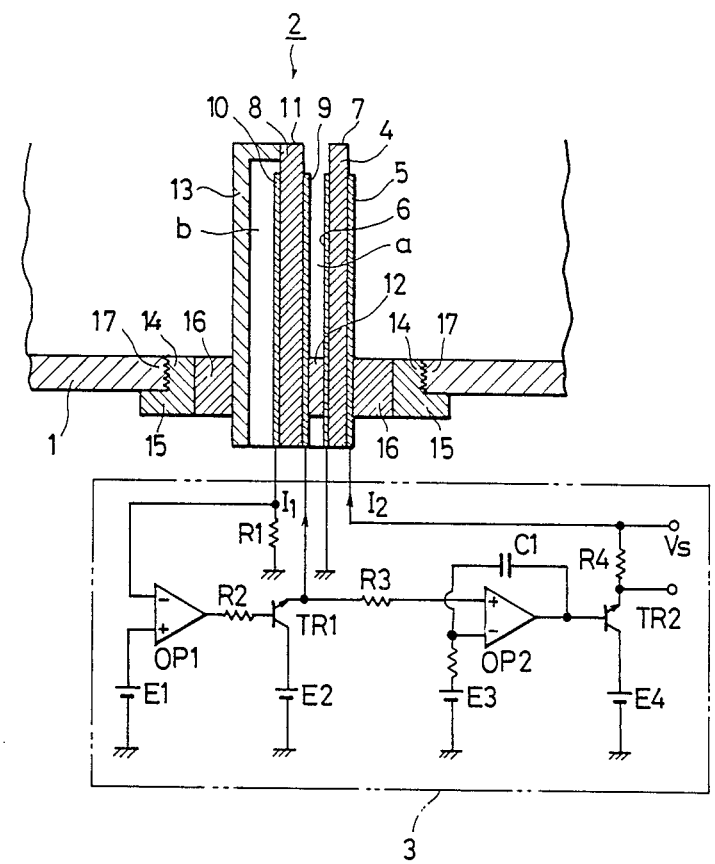
FIG. 1 shows diagrammatically the general layout of an A/F ratio detector constructed according to a preferred embodiment of the present invention.

The oxygen-ion-conductive solid electrolyte used in the present invention is typically made of a solid solution of zirconia and yttria or of zirconia and calcia. Also usable are solid solutions of cerium dioxide, thorium dioxide and hafnium dioxide; a solid solution of an oxide of the perovskite type; and a solid solution of a trivalent metal oxide.

The porous electrode to be formed on both sides of this solid electrolyte may be made of platinum, rhodium or any other metal that can catalyze the oxidative reaction. Preferred methods for forming the porous electrode include the following: A powder of one of the metals listed above (major component) is mixed with a powder of a ceramic material that is the same as that of the solid electrolyte. The mixture is processed into a paste form, which then is printed on the solid electrolyte plate by a suitable thick film forming technique and subsequently sintered. Alternatively, the electrode layer can be formed by a thin-film technique, for example, flame spraying, chemical plating or vapor deposition, and a porous protective layer made of alumina, spinel, zirconia, mullite, etc., is then formed on the electrode layer by a suitable thick-film technique. It is particularly preferred that the porous layer on the electrode facing the diffusion compartment be impregnated with a dispersion of platinum, rhodium, etc., to enhance the ability to catalyze oxidative reactions.

In accordance with the present invention, two elements are formed by the aforementioned procedures, and one of them is used as an oxygen-concentration-difference-actuated electrochemical cell.

The operating principle of the cell is as follows: If the oxygen ion-conductive solid electrolyte is placed under suitable temperature conditions (at least 400° C. if the solid electrolyte is zirconia), oxygen ions will migrate through the solid electrolyte from the surface where high oxygen partial pressures prevail to the area where the oxygen partial pressure is low, and the differential oxygen partial pressure across the solid electrolyte can be detected as a voltage (electromotive force) between the $O_2$ permeable electrodes provided on the opposite sides of the electrolyte.

In the detector of the present invention, an air compartment is formed in such a manner that the electrode provided on the side of the electrochemical cell opposite to the side facing the diffusion compartment contacts the atmosphere, which enables the generation of a voltage indicative of the difference between the concentration of atmospheric oxygen and that of oxygen present in the diffusion compartment.

The other of the two elements is used as an oxygen pump. Its operation depends on the ability of the oxygen-ion-conductive solid electrolyte to permit migration of oxygen ions through the electrolyte upon application of a voltage. When a voltage is applied between its two electrodes, this element pumps oxygen from the diffusion compartment into the exhaust gas. An air compartment may also be provided for the oxygen pump element on the side opposite to that facing the diffusion compartment, which arrangement is also within the scope of the present invention.

Therefore, the A/F ratio signal detector of the invention can produce an A/F ratio signal indicative of the concentration of oxygen in the exhaust gas by one of the following mechanisms: (1) Oxygen is pumped out of the diffusion compartment by the pump element at such a rate that the voltage generated by the electrochemical cell is held at a predetermined value, and the current flowing through the pump element (this current is hereunder sometimes referred to as the pump current) is detected. (2) Alternatively, the pump current flowing through the oxygen pump element can be held at a constant level so that oxygen is pumped out of the diffusion compartment at a predetermined rate, and the voltage generated by the electrochemical cell detected.

Figure 2:
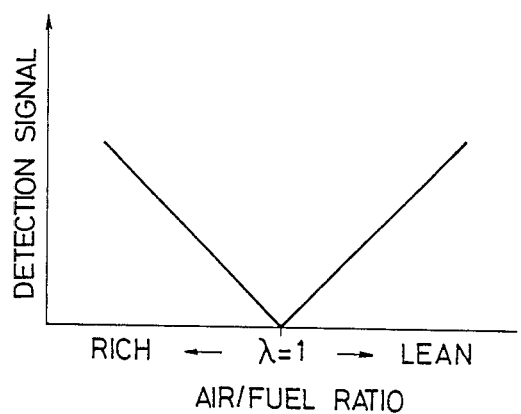
FIG. 2 is a diagram illustrating the characteristic of a detection signal produced by a conventional A/F ratio detector.
Figure 3:
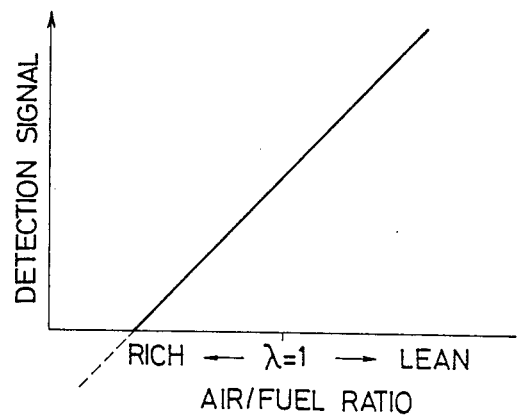
FIG. 3 is a diagram showing the characteristic of a detection signal produced by the A/F ratio detector of the present invention.

The purpose of providing the constant current supply is to use the element having the associated air compartment not only as an oxygen-concentration- difference-actuated electrochemical cell but also as an oxygen pump so that atmospheric oxygen can be pumped into the diffusion compartment at a predetermined rate. By supplying oxygen at a predetermined rate into the diffusion compartment, the following two advantages result: (1) First, no phenomenon such as is depicted in FIG. 2 will occur (i.e., the detection signal produced is reversed at an A/F ratio in the neighborhood of the theoretical value, giving rise to an ambiguous detection signal with respect to the fuel-rich and fuel-lean regions). (2) Secondly, a characteristic as shown in FIG. 3 is obtained (the A/F ratio indicating signal is an unambiguous, continuous detection signal throughout the operating range, i.e., in both the fuel-rich and fuel-lean regions).

Stated more specifically, the voltage applied to the electrochemical cell for causing a predetermined current to flow therethrough varies with the voltage generated in accordance with the differential oxygen concentration between the atmosphere and the diffusion compartment; therefore, an A/F ratio signal that is uniquely associated with a certain A/F ratio can be detected by one of the following two methods: (1) The pump current flowing through the oxygen pump element is controlled so as to hold the applied voltage at a constant value, and the corresponding value of the pump current is detected. (2) A constant current is passed through the electrochemical cell for a predetermined period of time so as to supply a predetermined amount of atmospheric oxygen into the diffusion compartment, and thereafter the voltage generated by the electrochemical cell or the pump current flowing through the oxygen pump element is controlled as explained before, and the corresponding value of either one of these two parameters is detected.

Two preferred embodiments of an A/F ratio detector of the present invention are hereunder described with reference to the accompanying drawings.

FIG. 1 shows diagrammatically the detector according to the first preferred embodiment of the invention. In this Figure, reference numeral 1 denotes an exhaust pipe from an internal combustion engine, 2 is the sensor unit of the detector mounted in the exhaust pipe 1, and 3 is an A/F ratio signal detector circuit for detecting an A/F ratio signal indicative of the concentration of oxygen in the exhaust gas. This detector circuit 3 corresponds to the A/F ratio signal detector.

The sensor unit 2 includes an oxygen pump element 7 and an oxygen-concentration-difference-actuated electrochemical cell 11. The pump element 7 consists of an oxygen-ion-conductive solid electrolyte plate 4 (about 0.5 mm thick and preferably made of stabilized zirconia) having two porous Pt electrode layers 5 and 6 formed on the opposite sides of the plate 4. Each Pt layer has a thickness of about 20 microns, and may be formed by a thick-film deposition technique. The electrochemical cell 11 also consists of an oxygen-ion-conductive solid electrolyte plate 8 which, like the pump element 7, is provided with two porous Pt electrode layers 9 and 10 on its opposite sides. The pump element 7 and the electrochemical cell 11 are mounted side by side in the exhaust pipe 1 with a gap (corresponding to the diffusion compartment described above) therebetween, the gap a being typically about 0.1 mm, and preferably 0.05 to 0.15 mm, in width. The two elements are fixed together by filling the gap at the base portion with a heat-resistive and insulating spacer 12. That side of the electrochemical cell 11 which is opposite the side facing the gap is provided with a wall 13 made of a heat-resistant and gas-impermeable material (typically a metal or ceramic) so as to define an air compartment b that establishes contact between the atmosphere and the porous Pt electrode layer 10. A support 15 with a male thread 14 is fixed around the base portion of the combination of the pump element 7, electrochemical cell 11 and wall 13 by means of a heat-resistant and insulating adhesive member 16. The sensor unit 2 having the construction described above is securely mounted in the exhaust pipe 1 by engaging the male thread 14 with a female thread 17 formed in the exhaust pipe 1.

In the A/F ratio signal detector circuit 3, the current flowing through the electrochemical cell 11 is controlled to be at a constant level so that atmospheric oxygen at a given rate is pumped from the air compartment b to the gap a. Also, the pump current flowing through the pump element 7 is controlled so that the voltage applied to the electrochemical cell 11 (this applied voltage varies with the electromotive force generated in response to the differential oxygen concentration between the gap a and the air compartment b) is maintained at a predetermined value. The corresponding value of the pump current is detected at the A/F ratio signal.

The porous Pt electrode layer 10 formed on that side of the electrochemical cell 11 which faces the air compartment b is connected to the inverting input terminal of an operational amplifier OP1 and grounded through a resistor R1. The other porous Pt electrode 9 facing the gap a is connected to the emitter of a transistor TR1, the base of which is connected to the output terminal of the operational amplifier OP1 through a resistor R2. The noninverting input terminal of the amplifier OP1 and the collector of the transistor TR1 are supplied with predetermined bias voltages E1 and E2, respectively. By the combined operation of OP1 and TR1, the emitter voltage of the transistor TR1 is controlled so that the voltage applied to the porous Pt electrode layer 10 is made equal to E1, and a constant current I1 determined by E1/R1 flows through the electrochemical cell 11.

The output terminal of the amplifier OP1 is connected to the non-inverting input terminal of an operational amplifier OP2 through a resistor R3, while the inverting input terminal of OP2 is supplied with a predetermined bias voltage E3. The non-inverting input terminal of the amplifier OP2 is connected to its output terminal by a capacitor C1. In other words, the amplifier OP2 is operated as an integrator circuit. The output terminal of the amplifier OP2 is further connected to the base of an NPN transistor TR2, which is supplied with a predetermined bias voltage E4 at its collector. The emitter of the transistor TR2 is connected to the porous electrode layer 5 (formed on the side of the pump element 7 opposite the side facing the gap a) through a resistor R4, while the porous electrode layer 6 facing the gap a is directly grounded. In this circuit, the voltage at the output terminal of the amplifier OP1 (or the voltage applied to the electrochemical cell 11) is compared with the voltage E3 by the operational amplifier OP2 and the detected difference is applied, via the transistor TR2, as a reference for the purpose of controlling the pump current I2 flowing through the oxygen pump element 7.

The foregoing description can be summarized as follows: The output voltage of the amplifier OP1 that is applied to the electrochemical cell 11 in order to pump atmospheric oxygen into the gap a at a certain rate varies with the voltage (electromotive force) generated in response to the differential oxygen concentration between the air compartment b and the gap a, and the greater this electromotive force, the smaller the voltage produced at the output of the amplifier OP1 (and vice versa). The pump current I2 flowing through the oxygen pump element 7 is controlled so as to hold this output voltage at a constant level. In accordance with the present invention, the voltage Vs across the resistor R4 through which the pump current I2 flows is detected, thereby to obtain a signal that is uniquely associated with a particular A/F ratio, as shown in FIG. 3.

In the first preferred embodiment of the present invention described above, the pump current I2 flowing through the oxygen pump element is controlled so that a constant voltage is produced at the output terminal of the amplifier OP1, which causes a constant current to flow into the electrochemical cell 11, and with a constant voltage present at the output of the amplifier OP2, the value of the pump current is detected. In this case, the voltage generated by the cell 11 as a result of the change in the A/F ratio may be so small as compared with the output voltage of the amplifier OP1, and hence considerable difficulty may be encountered in detecting a change in A/F ratio. In order to avoid this difficulty, the voltage between the porous Pt electrode layers 9 and 10 on the electrochemical cell 11 may be detected by a differential amplifier, and the pump current controlled so that the detected voltage is held constant. If this is done, the corresponding value of the pump current can be readily detected. This modification will ensure precise production of an A/F ratio signal.

An A/F ratio detector according to a second preferred embodiment of the present invention may be constructed using the sensor unit 2 of the same type as that employed in the aforementioned first preferred embodiment. Further, in the second embodiment, the following two operations are performed cyclically at given intervals: (1) First, the electrochemical cell 11 is used to pump a predetermined amount of atmospheric oxygen into the gap a. (2) Secondly, the electromotive force generated by the cell 11 is detected and the pump current flowing through the oxygen pump element 7 is controlled so as to maintain the detected electromotive force at a constant level. The corresponding value of the pump current is then employed as an A/F ratio signal.

Figure 4:
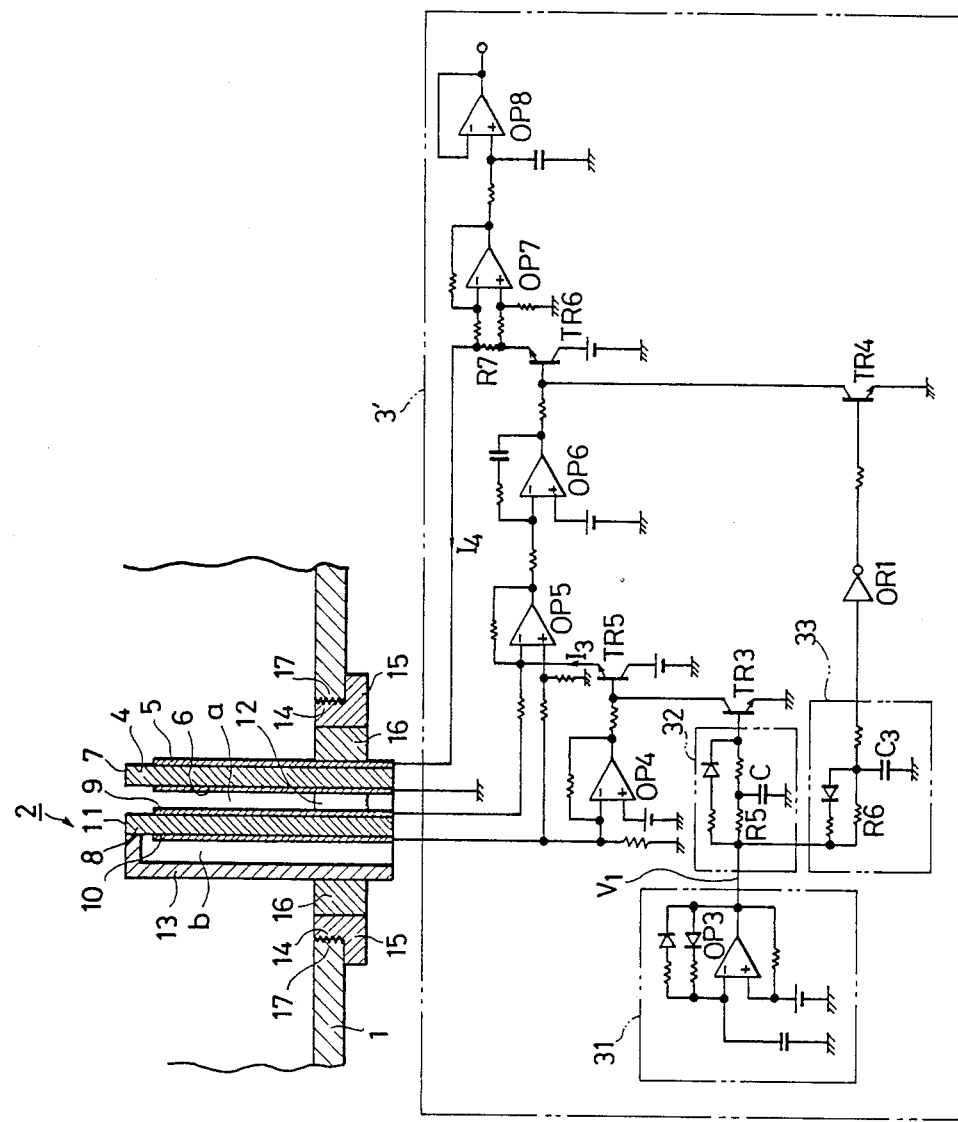
FIG. 4 shows diagrammatically the general layout of the A/F ratio detector according to another embodiment of the present invention.

FIG. 4 shows diagrammatically the general layout of the detector of the second preferred embodiment of the present invention. As already mentioned, the sensor unit 2 is completely identical with the one employed in the first preferred embodiment.

In FIG. 4, reference numeral 31 denotes a multivibrator including principally an operational amplifier OP3. The multivibrator produces pulse signals at predetermined time intervals. Reference numeral 32 indicates a time-constant circuit connected to the base of a transistor TR3. With this circuit, the transistor TR3 turns on simultaneously with the rise of a pulse signal V1 delivered from the multivibrator 31, whereas TR3 is turned off at a time delayed from the fall of V1 by a time t1 (see FIG. 5) determined by the values of a resistor R5 and a capacitor C2. Reference numeral 33 identifies a time-constant circuit connected to the base of a resistor TR4 through an OR gate OR1. In this circuit, the transistor TR4 is turned off at a time delayed from the rise of V1 by a time t2 (see FIG. 5) determined by the values of a resistor R6 and a capacitor C3, whereas TR4 will be turned on simultaneously with the fall of V1.

Figure 5:
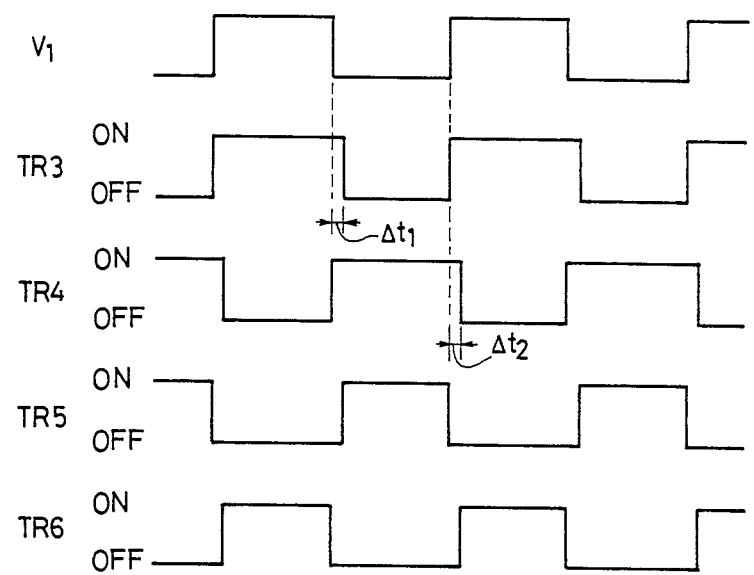
FIG. 5 is a timing chart illustrating the operation of the detector of FIG. 4.

An operational amplifier OP4 combined with a transistor TR5 provides a constant-current circuit used to cause a predetermined amount of current I3 to flow through the electrochemical cell 11 to pump oxygen at a predetermined rate from the atmosphere into the gap a. The base of the transistor TR5 is connected to the collector of TR3. Thus, when the transistor TR3 is off, TR5 will conduct, as shown in FIG. 5, whereby the predetermined current I3 will flow through the electrochemical cell 11.

An operational amplifier OP5 provides an amplifier circuit for amplifying the voltage generated across the electrochemical cell 11, which voltage is representative of the differential oxygen concentration between the atmosphere and the gap a. An operational amplifier OP6 combined with a transistor TR6 provides a pump current control circuit that controls a current I4 flowing through the oxygen pump 7 so that the differential $O_2$ concentration indicating voltage signal amplified by the amplifier OP5 will be always be held at a predetermined level. Since the base of the transistor TR6 is connected to the collector of the transistor TR4, control of the pump current I4 is performed when the electrochemical cell 11 is not operating as a pump element. In other words, the transistor TR6 conducts to perform the pump current controlling action only while the transistor TR4 remains off, as shown in FIG. 5.

An operational amplifier OP7 (a differential amplifier) is provided for detecting the pump current 14 flowing through the oxygen pump element 7 by detecting the voltage drop across a resistor R7. The voltage signal from the amplifier OP7 is smoothed by the combination of a capacitor C2 and an operational amplifier OP8 and detected as an A/F ratio signal Vs.

In the second preferred embodiment described above, the electrochemical cell 11 is alternately used as an oxygen pump element and as an oxygen-concentration-difference-actuated electrochemical cell, and an A/F ratio signal is detected after a predetermined amount of oxygen has been pumped into the gap a. This technique is effective for the purpose of cancelling any adverse effects of impedance variations resulting from the electrochemical cell 11. The characteristics of the A/F ratio signal obtained have the profile shown in FIG. 3, the signal being uniquely associated with a certain A/F ratio over the full operating range, including both the fuel-lean and fuel-rich regions.

As described above, the A/F ratio detector of the present invention is characterized by the provision of two features: (1) an air compartment that ensures contact between the atmosphere and the electrode formed on that side of the oxygen-concentration-difference-actuated electrochemical cell opposite to the side facing the diffusion compartment, and (2) a constant current supply that enables the electrochemical cell to operate not merely as a device for generating an electromotive force indicative of the differential oxygen concentration between the atmosphere and the diffusion compartment, but also as a pump element that is supplied with a predetermined amount of current so as to pump atmospheric oxygen at a predetermined rate into the diffusion compartment. Using the detector of the present invention, an A/F ratio signal is obtained int he form of a continuous and unidirectional electrical quantity over the full operating range, including both the fuel-lean and fuel-rich regions, which enables simple detection of the A/F ratio of the air fuel mixture being supplied to the associated internal combustion engine or other burner device. The A/F ratio signal detected by the system of the present invention may be directly used for ensuring simple and precise control of the A/F ratio over the full operating range, including the fuel-lean region, the theoretical A/F ratio, and the fuel-rich region.

We claim:

1. An A/F ratio detector for providing continuous unidirectional detection signal indicative of the A/F radio in combustion gases over the detector's entire operating region, including both a fuel-rich region and a fuel-lean region, comprising:
   (1) a sensor unit comprising two elements, each of said two elements comprising an oxygen ion-conductive solid electrolyte having a respective porous electrode formed on both surfaces, said two elements being disposed to each face a diffusion compartment between said elements which receives a limited inflow of exhaust gas; and
   (2) A/F ratio signal detecting means for operating one of said two elements as an oxygen-concentration-difference-actuated electrochemical cell and the other as an oxygen pump cell, said detecting means comprising means for controlling a predetermined one of a voltage produced by said electrochemical cell and a current flow through said pump cell so as to produce a continuous, unidirectional A/F ratio detection signal indicative of a concentration of oxygen in said exhaust gas, said sensor unit further comprising means for defining an air compartment, said electrochemical cell contacting the atmosphere at the one of its electrodes disposed opposite to said diffusion compartment, and said A/F ratio signal detecting means comprising constant current supplying means for supplying a predetermined current to said electrochemical cell so that oxygen is pumped at a predetermined rate from the atmosphere into said diffusion compartment by means of said electrochemical cell, the electrode of said oxygen pump cell disposed opposite to said diffusion compartment directly facing said exhaust gas.

2. The A/F ratio detector of claim 1, further comprising means for controlling a current flowing between said electrodes of said pump cell in accordance with a voltage produced across said electrodes of said electrochemical cell such that said voltage produced across said electrodes of said electrochemical cell is constant.

3. The A/F ratio detector of claim 2, further comprising means for producing as an output A/F ratio detector signal representative of a concentration of oxygen in said exhaust a signal representative of said current flowing between said electrodes of said pump cell.

4. The A/F ratio detector of claim 1, further comprising means for alternating operating said constant current supplying means and said current controlling means so that operations of (1) said electrochemical cell pumping a predetermined amount of oxygen into said diffusion compartment and (2) producing a signal representing said A/F ratio are alternated.

5. An A/F ratio detector for providing a continuous unidirectional detection signal indicative of the A/F ratio in combustion gases over the detector's entire operating region, including both a fuel-rich region and a fuel-lean region, comprising:
   (1) a sensor unit comprising two elements, each of said two elements comprising an oxygen ion-conductive solid electrolyte having a porous electrode formed on both surfaces, said elements being disposed to face a diffusion compartment which receives a limited inflow of exhaust gas;
   (2) A/F ratio signal detecting means for operating one of said two elements as an oxygen-concentration-difference-actuated electrochemical cell and the other as an oxygen pump cell, said detecting means comprising means for controlling a predetermined one of a voltage produced by said electrochemical cell and a current flow through said pump cell so as to produce a continuous, unidirectional A/F ratio detection signal indicative of a concentration of oxygen in said exhaust gas, said sensor unit further comprising means for defining an air compartment, said electrochemical cell contacting the atmosphere, through said air compartment, at the one of its electrodes disposed opposite to the side facing said diffusion compartment, and said A/F ratio signal detecting means comprising constant current supplying means for supplying a predetermined current to said electrochemical cell so that oxygen is pumped at a predetermined rate from the atmosphere into said diffusion compartment by means of said electrochemical cell;

(3) means for controlling a current flowing between said electrodes of said pump cell in accordance with a voltage produced across said electrodes of said electrochemical cell such that said voltage produced across said electrodes of said electrochemical cell is constant; and (4) means for producing, as an output A/F ratio detection signal representative of a concentration of oxygen in said exhaust, a signal representative of said current flowing between said electrodes of said pump cell, wherein said means for supplying a predetermined current to said electrochemical cell comprises: a first reference voltage source having a first terminal coupled to ground; a first operational amplifier having a first input terminal coupled to one of said electrodes of said electrochemical cell and a second input terminal coupled to a second terminal of said first reference voltage source; a first resistor coupled between said one of said electrodes of said electrochemical cell and ground; a second reference voltage source having a first terminal coupled to ground; and a first transistor having a base coupled to an output of said first operational amplifier, a collector coupled to a second terminal of said second reference voltage source, and an emitter coupled to the other of said electrodes of said electrochemical cell.

6. The A/F ratio detector of claim 5, wherein said means for controlling said current flowing between said electrodes of said pump cell comprises: a third reference voltage source having a first terminal coupled to ground; a second operational amplifier having a first input terminal coupled to said emitter of said first transistor and a second input coupled to a second terminal of said third reference voltage source; a fourth reference voltage source having a first terminal coupled to ground; and a second transistor having a base coupled to an output of said second operational amplifier, a collector coupled to a second terminal of said fourth reference voltage source, and an emitter coupled to one of said electrodes of said pump cell, the other of said electrodes of said pump cell being coupled to ground.

7. The A/F ratio detector of claim 6, wherein said output signal producing means comprises a second resistor coupled between said emitter of said second transistor and said one electrode of said pump cell.

8. The A/F ratio detector of claim 5, further comprising means for alternating operating said constant current supplying means and said current controlling means so that operations of (1) said electrochemical cell pumping a predetermined amount of oxygen into said diffusion compartment and (2) producing a signal representing said A/F ratio are alternated.

9. The A/F ratio detector of claim 8, wherein said alternating operating comprises: multivibrator means having first and second alternating activated output terminals, said first output terminal being coupled to the base of said first transistor and said second output terminal being coupled to the base of said second transistor; and a third operational amplifier having first and second input terminals coupled to said electrodes of said electrochemical cell and an output coupled to said first input terminal of said second operational amplifier.

10. The A/F ratio detector of claim 9, further comprising first and second directional time constant circuit means coupled, respectively, in series between with first and second output terminals of said multivibrator means.

11. The A/F ratio detector of claim 10, wherein said means for producing said output signal comprises: a fourth operational amplifier having first and second terminals coupled across said second resistor; a fifth operational amplifier having an input terminal coupled to an output of said fourth operational amplifier; and smoothing circuit means coupled to said fifth operational amplifier.

12. An A/F ratio detector for providing a continuous unidirectional detection signal indicative of the A/F ratio in combustion gases over the detector's entire operation region, including both a fuel-rich region and a fuel-lean region, comprising:

(1) a sensor unit comprising two elements, each of said two elements comprising an oxygen ion-conductive solid electrolyte having a respective porous electrode formed on both surfaces, said elements being disposed to each face a diffusion compartment which receives a limited inflow of exhaust gas;

(2) A/F ratio signal detecting means for operating one of said two elements as an oxygen-concentration-difference-actuated electrochemical cell and the other as an oxygen pump cell, said detecting means comprising means for controlling a predetermined one of a voltage produces by said electrochemical cell and a current flow through said pump cell so as to produce a continuous, unidirectional A/F radio detection signal indicative of a concentration of oxygen in said exhaust gas, said sensor unit further comprising means for defining an air compartment, said electrochemical cell contacting the atmosphere, through said air compartment, at the one of its electrodes disposed opposite to said diffusion compartment, and said A/F ratio signal detecting means comprising constant current supplying means for supplying a predetermined current to said electrochemical cell so that oxygen is pumped at a predetermined rate from the atmosphere into said diffusion compartment by means of said electrochemical cell, the electrode of said oxygen pump disposed opposite to the diffusion compartment directly facing the exhaust gas;

(3) means for controlling a current flowing between said electrodes of said pump cell in accordance with a voltage produced across said electrodes of said electrochemical cell such that said voltage produced across said electrodes of said electrochemical cell is constant; and (4) means for producing, as an output A/F ratio detection signal representative of a concentration of oxygen in said exhaust gas, a signal representative of said current flowing between said electrodes of said pump cell.

13. An A/F ratio detector according to claim 12, wherein said means for supplying a predetermined current to said electrochemical cell comprises: means for sensing a current passing through one of said electrodes of said electrochemical cell; and a controllable current source connected to one of said electrodes of said electrochemical cell and controlled by an output of said sensing means.

14. The A/F ratio detector of claim 13, wherein said controllable current source comprises a transistor and a voltage source connected in series to a second one of said electrodes of said electrochemical cell, a control electrodes of said transistor of said controllable current source being controlled by an output of said sensing means.

* * * * *